(12) United States Patent
Becker et al.

(10) Patent No.: US 6,190,898 B1
(45) Date of Patent: Feb. 20, 2001

(54) CRYSTALLINE CELLULASE AND METHOD FOR PRODUCING SAME

(75) Inventors: Nathaniel T. Becker, Burlingame, CA (US); Edit L. Braunstein, Rochester; Robert Fewkes, Webster, both of NY (US); Ernst H. Gros, Kantvik (FI); Meng H. Heng, Rochester, NY (US)

(73) Assignee: Genencor International, Inc., Palo Alto, CA (US)

( * ) Notice: Under 35 U.S.C. 154(b), the term of this patent shall be extended for 0 days.

(21) Appl. No.: 08/609,362

(22) Filed: Mar. 1, 1996

Related U.S. Application Data

(63) Continuation-in-part of application No. 08/547,096, filed on Oct. 23, 1995, now abandoned.

(51) Int. Cl.$^7$ ........................................................ C12N 9/14
(52) U.S. Cl. ............................ 435/200; 435/195; 435/201
(58) Field of Search ...................................... 435/195, 200, 435/201

*Primary Examiner*—Leon B. Lankford, Jr.
(74) *Attorney, Agent, or Firm*—Genencor International, Inc.

(57) ABSTRACT

A method for preparing a crystalline cellulase enzyme is provided which comprises preparing an aqueous solution containing cellulase enzyme and adding to the aqueous solution a salt comprising an anion selected from the group consisting of sulfate, phosphate, formate, acetate, sorbate, chloride, bromide, fluoride or iodide, and a cation selected from the group consisting of sodium, ammonium, magnesium, potassium or calcium, wherein the aqueous solution is at a temperature between 10° C. and 60° C.

32 Claims, 1 Drawing Sheet

CRYSTALLINE CELLULASE AND METHOD FOR PRODUCING SAME

CROSS-REFERENCE TO RELATED APPLICATIONS

This application is a continuation-in-part of U.S. application Ser. No. 08/547,096 filed Oct. 23, 1995 now abandoned, and which is incorporated herein by reference in its entirety.

BACKGROUND OF THE INVENTION

The present invention is related to the crystallization of cellulase enzymes. More particularly, the present invention relates to selective crystallization using salt of cellulase enzymes in an aqueous solution produced by, for example, the fermentation of microbial organisms such as filamentous fungi, yeast or bacteria.

Intensive research efforts have been directed to the precipitation and crystallization of enzymes as a means of purification and preparation of enzyme products. For example, in U.S. Pat. No. 4,659,667, a process is disclosed for the recovery of an enzyme from solution by concentrating to supersaturation the enzyme-containing solution at pH near the isoelectric point of the enzyme, inducing crystallization and recovering the crystallized final product. Inducing crystallization is achieved by allowing the enzymes to spontaneously crystallize upon concentration or by seeding, sound, stirring or scratching the inner surface of the container. Crystallization of alpha-amylase is exemplified.

In PCT Publication No. WO 89/08703, a process is described for the crystallization of subtilisin by adding a halide salt, such as sodium chloride or calcium chloride, to a concentrated subtilisin solution of at least about 40 grams per liter at temperatures less than 10° C.

In PCT Publication No. WO 91/09943, a method for the crystallization of enzymes is disclosed which is characterized by using as a starting material an aqueous solution containing liquid with a relatively high enzyme purity and a concentration of enzyme of about at least 5 grams per liter and adding as a crystallization agent an easily soluble salt of the non-halide type to a concentration which is considerably smaller than the amount necessary to precipitate the enzymes in an amorphous form. Crystallization of certain subtilisin enzymes is exemplified.

In EP 549,048, a method for the preparation of highly purified alkaline protease from *Bacillus licheniformis* or *Bacillus alcalophilus* is disclosed which is characterized by adding hydrolytic enzymes and sodium chloride to concentrated alkaline protease, incubating the mixture at a temperature above 20° C. to separate the alkaline protease from hydrolyzed polymeric impurities and collecting the purified precipitate. However, the precipitate was predominantly amorphous.

Methods for preparing cellulase crystals for the purpose of x-ray crystallography have been successful on a small scale. For example, Bergfors et al., J. Mol. Biol., vol. 209, no. 1, pp. 167–169 (1989) illustrate crystallization using the hanging drop method of the core protein of cellobiohydrolase II from *Trichoderma reesei* and subsequent study of the crystals to determine tertiary structure. In Wilson, Crit. Rev. Biochem., vol. 12(1/2), pp. 45–63 (1992) the 30 K catalytic subunit of the E2 cellulase from *T. fusca* was crystallized using ammonium sulfate as a precipitant to determine the tertiary structure. Importantly, Wilson points out that the numerous attempts to crystallize the *T. fusca* cellulases E2, E3 and E5 in the prior art using the hanging drop method with both ammonium sulfate and polyethylene glycol had failed. Thus, although crystallization of certain enzymes has been successful according to the means described above, the crystallization of cellulases has remained problematic with no known method for such crystallization on a large scale basis.

In spite of these advances in the field of enzyme crystallization in general, and occurrences of crystallization of cellulases, reported in the scientific literature, for the purpose of crystallographic studies, inexpensive and efficient crystallization of cellulase enzymes suitable for large scale production has remained problematic in industry. In fact, no commercially feasible process has been described for the crystallization of cellulases in terms of producing a low cost, high yield, rapid and highly purified cellulase enzyme in a simple manner.

To the contrary, Applicants have discovered that the employment of a specific group of salts and a specific temperature range provides the capability of selectively purifying through crystallization a commercially important subgroup of cellulases (i.e., those which lack a distinct cellulose binding domain) over other cellulases which possess a cellulose binding domain.

Further, any protein can be precipitated with enough salt, however, the industry prefers crystalline enzymes for further processing into, i.e., granules or immobilized enzymes. The present invention provides methods of obtaining a cellulase enzyme product.

BACKGROUND OF THE INVENTION

It is an object of the present invention to provide for a simple and low-cost method which selectively crystallizes cellulases which lack a cellulose binding domain using specific salts.

It is an object of the invention to produce a cellulase enzyme.

According to the present invention, a method for the crystallization of cellulase enzyme which lacks a cellulose binding domain is provided comprising (a) preparing an aqueous solution containing the cellulase enzyme; and (b) adding to the aqueous solution a salt comprising an anion selected from the group consisting of sulfate, phosphate, formate, acetate, sorbate, chloride, bromide, fluoride or iodide, and a cation selected from the group consisting of sodium, ammonium, magnesium, potassium or calcium, or a mixture thereof. In a preferred embodiment, the aqueous solution is at a temperature above 4° C. In a preferred embodiment, the anion is selected from the group consisting of sulfate, acetate and chloride, and the cation is selected from the group consisting of sodium, ammonium or magnesium.

Applicants have surprisingly discovered that the crystallization kinetics for cellulase enzymes are improved when the crystallization takes place at a temperature above 4° C. As such, crystallization can take place at room temperature and significant savings are available in terms of equipment and energy.

Through the practice of the present invention, it is possible to obtain in an unexpectedly short period of time a highly purified cellulase enzyme product which has exceptional yield characteristics. In fact, by optimizing conditions according to the present invention, it is often possible to obtain consistent yields of greater than 50%, and in a particularly preferred embodiment, yields of greater than 70–80% in a period of five hours. This result is of great value to the industry.

In practicing the present invention, Applicants have surprisingly discovered that cellulases which lack a cellulose binding domain are characterized by more favorable crystallization kinetics than cellulases which possess a cellulose binding domain. As a result, an unexpected advantage is achieved by the practice of the present invention whereby cellulases which lack a cellulose binding domain can be easily crystallized in comparison with cellulases which possess a cellulose binding domain allowing for selective crystallization out of solution of only the cellulases which possess a cellulose binding domain. In the practice of the present invention, for the first time an easily reproducible method for preparing a highly purified and crystalline product from an industrially important subgroup of cellulase enzymes, i.e., those without cellulose binding domains, has become available. Such a result is a surprising and advantageous advance in the art of crystallization and solves a long standing problem in the field.

Another advantage of the present invention is the surprising discovery that the crystallized cellulase enzymes produced according to the present invention results in reduced backstaining in textile applications, such as stonewashing, over other cellulases produced by other methods. Examples of processes utilizing cellulase which will benefit from the present method of purification includes methods for the treatment of textiles described in PCT Publication No. WO 92/06221.

Yet another advantage of the present invention is that the crystallization process occurs very quickly. In contrast to many prior art processes which often require as much as 2–3 weeks for the crystallization of cellulase enzyme, the instant invention produces a high yield of highly purified cellulase crystals in as little as 5 hours.

DETAILED DESCRIPTION OF THE INVENTION

Figure 1:
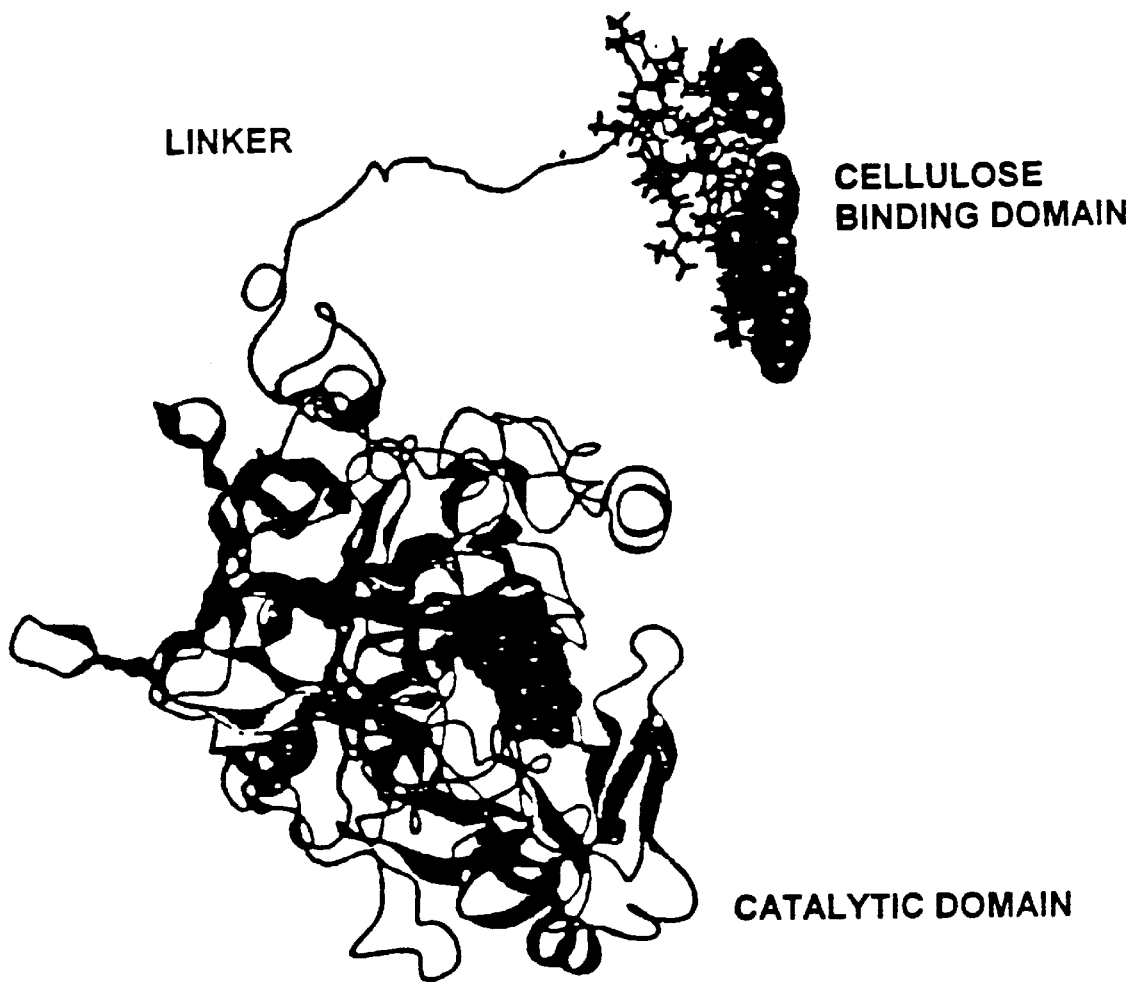
FIG. 1 illustrates the proposed tertiary structure of an exocellobiohydrolase enzyme derived from *Trichoderma longibrachiatum* (CBHI) showing the catalytic domain which is connected via the linker to the cellulose binding domain.

"Cellulase," "cellulolytic enzymes" or "cellulase enzymes" means bacterial, plant or fungal exoglucanases or exocellobiohydrolases, endoglucanases, and β-glucosidases. These three different types of cellulase enzymes act synergistically to convert cellulose and its derivatives to glucose. A cellulase composition produced by a naturally occurring source and which comprises one or more cellobiohydrolase-type and endoglucanase-type components wherein each of these components is found at the ratio produced by the source is sometimes referred to as a "complete cellulase system" or a "complete cellulase composition" to distinguish it from the classifications and components of cellulase isolated therefrom, from incomplete cellulase compositions produced by bacteria and some fungi, or from a cellulase composition obtained from a microorganism genetically modified so as to overproduce, underproduce, or not produce one or more of the cellobiohydrolase-type and/or endoglucanase-type components of cellulase. The different components, i.e., the various endoglucanases and exocellobiohydrolases in a whole cellulase or incomplete multicomponent cellulase, generally have different properties, such as isoelectric point, molecular weight, degree of glycosylation, substrate specificity and enzymatic action patterns.

The term "cellulose binding domain" refers herein to a peptide or group of related peptides responsible in large part for the cellulose binding activity of a cellulase or derivative thereof. Cellulose binding domains generally function by non-covalently binding the cellulase to cellulose, a cellulose derivative or other polysaccharide equivalent of cellulose. Cellulose binding domains as defined herein are believed to attach the enzyme to cellulose in a manner which permits or facilitates hydrolysis of cellulose fibers by the structurally distinct catalytic core region, but nonetheless functioning in an independent manner from the catalytic core. Thus, a cellulose binding domain will not possess the significant hydrolytic activity attributable to a catalytic core. Moreover, the cellulose binding domain as defined herein should be distinguished from a cellulose binding region which is integral to an enzymatic subunit which possesses catalytic activity. While such a cellulose binding region can, in fact, provide some cellulose binding activity, such a feature of a cellulase would not be equivalent to a cellulose binding domain, which domain is a distinct structural feature of the enzyme. In other words, a cellulose binding domain is a structural element of the cellulase enzyme protein tertiary structure which is distinct from the structural element which possesses catalytic activity. For illustrative purposes, an example of a cellulase incorporating a cellulose binding domain as defined herein is provided in FIG. 1. Analysis of the genes coding for CBHI, CBHII, EGI, EGII and EGV in *Trichoderma longibrachiatum* shows a domain structure comprising a catalytic core region or domain (CCD) and a hinge or linker region (used interchangeably herein) which connects the catalytic core region to a cellulose binding domain (CBD).

While not wishing to be bound by theory, it is believed that the cellulose binding domain interferes with the crystallization of cellulases in part due to its tertiary structure, which is believed to protrude from the main body of the enzyme, and because of the flexibility of the binding domain as conferred by the linker region. These characteristics can result in significantly unfavorable crystallization kinetics, and thus prevent the crystallization of many cellulases. "Linker or hinge region" means a short peptide region that links together structurally distinct catalytic core and cellulose binding domains of a cellulase. These domains in *T. longibrachiatum* cellulases, for example, are linked by a peptide rich in Ser, Thr and Pro.

"Incubation" means the crystallization time or the time period after addition of salt to the aqueous solution.

In a preferred embodiment of the present invention, a method for the crystallization of cellulase enzyme which lack a cellulose binding domain is provided comprising preparing an aqueous solution containing said cellulase enzyme and adding to said aqueous solution a salt comprising an anion selected from the group consisting of sulfate, phosphate, formate, acetate, sorbate, chloride, bromide, fluoride or iodide, and a cation selected from the group consisting of sodium, potassium, ammonium, magnesium or calcium, or a mixture thereof. In a preferred embodiment, the aqueous solution is at a temperature above 4° C. In a more preferred embodiment, the cellulase further lacks a linker or hinge region.

The cellulase enzyme of the invention can be obtained from any cellulase producing microorganism wherein a produced cellulase lacks a cellulose binding domain. Cellulases which are preferably crystallized according to the present invention are bacterial, plant and fungal cellulases which lack a cellulose binding domain. More preferably, the fungal cellulases are derived from Trichoderma sp., including *Trichoderma longibrachiatum*, *Trichoderma viride*, *Trichoderma koningii*, Penicillium sp., Humicola sp., including *Humicola insolens*, Aspergillus sp. and Fusarium sp. As used herein, the term "Trichoderma" or "Trichoderma sp." refers to any fungal strains which have previously been classified as Trichoderma or which are currently classified as Trichoderma. Bacterial cellulases from Thermomonospora sp., Cellulomonas sp., Bacillus sp., Pseudomonas sp., Clostridium sp. and Streptomyces sp. are also preferred. Cellulases which lack a cellulose binding domain are known in the art. Naturally-occurring cellulases which lack a cellulose binding domain include, for example, bacterial cellulases derived from Erwinia carotovora (see, e.g., Saarilahti et al. Gene, Vol. 90, pp. 9–14 (1990)) and *Clostridium thermocellum* (see, e.g., Gilkes et al., Microbiological Reviews, pp. 303–315 (1991)).

Genetically modified cellulases which are derived from a DNA sequence in which all or part of the nucleotides in the coding region which encodes the cellulose binding domain have been deleted, replaced or otherwise manipulated to destroy the cellulose binding characteristics are also considered within the scope of the invention. Such modified cellulases are described in PCT Publication No. WO 95/16782. Thus, a cellulase belonging to the family of cellulases described in PCT Publication No. WO 91/17244, characterized by a highly conserved cellulose binding domain structure, could be modified by known genetic engineering methods to delete the DNA encoding for this region.

The fermentation procedures for culturing fungi and bacteria and for production of cellulase enzymes are known per se in the art. For example, cellulase enzymes can be produced either by solid or submerged culture, including batch, fed-batch and continuous-flow processes. The collection and purification of the cellulose enzymes from the fermentation broth can also be done by procedures known per se in the art.

The aqueous solution which acts as starting material for the method according to the invention is derived from the fermentation broth produced by the fermentation of an appropriate microorganism. The fermentation broth will generally contain cellular debris, including cells, various suspended solids and other biomass contaminants, as well as the desired cellulase enzyme product, which are preferably removed from the fermentation broth by means known in the art. Suitable processes for such removal include conventional solid-liquid separation techniques such as, e.g., centrifugation, filtration, dialysis, microfiltration, rotary vacuum filtration, or other known processes, to produce a cell-free filtrate. While it is contemplated as within the scope of the invention to crystallize the cellulase enzyme either directly from the fermentation broth or from the cell-free filtrate, it is preferable to further concentrate the fermentation broth or the cell-free filtrate prior to crystallization using techniques such as ultrafiltration, evaporation or precipitation.

It has long been known in the art that certain constituents, if included in a culture medium, will result in difficulty in crystallization of the component enzymes. For this reason, it is often advantageous to further purify the filtered fermentation broth to remove impurities which can interfere with crystallization by, for example, subjecting the filtered broth to column purification. Additionally, it is possible to limit the amount of such impurities by controlling the culture medium in which the microorganism is grown. For example, as described in Northrup et al., Crystalline Enzymes, Columbia University Press, p. 254 (1948) mucin-like substances, e.g., polysaccharides, are often detrimental to crystallization processes. Thus, by eliminating such polysaccharide components from the pre-fermentation culture medium or purifying such components from a fermentation broth, it is possible to improve the success of the subsequent crystallization. Alternatively, these substances can be removed by treatment of the filtrate with a strong acid, copper hydroxide, alcohol or acetone. Additionally, it is known that the addition of salts such as aluminum sulfate or other aluminum salts can be advantageous in purifying fermentation broths in order to facilitate crystallization.

After preparation of the aqueous solution containing cellulase enzyme, a salt is added to the aqueous solution, which is at a temperature above 4° C., preferably between 10° C. and 60° C., more preferably between 20° C. and 40° C. and most preferably between 22° C. and 37° C., to initiate crystallization of the cellulase enzyme which lacks a cellulose binding domain. The salt comprises an anion selected from the group consisting of sulfate, phosphate, acetate, formate, sorbate, chloride, bromide, fluoride or iodide, and a cation selected from the group consisting of sodium, potassium, ammonium, magnesium or calcium, or a mixture thereof. Preferably, the salt comprises sodium sulfate, ammonium sulfate, magnesium sulfate, sodium acetate, ammonium acetate, magnesium acetate, sodium chloride, ammonium chloride or magnesium chloride, or a mixture thereof. Most preferably, the salt comprises sodium sulfate. In a preferred embodiment, the cellulase concentration in the aqueous solution is between about 10 ONPC/ml and 300 ONPC/ml, more preferably between about 10 ONPC/ml and 150 ONPC/ml and most preferably between about 40 ONPC/ml and 60 ONPC/ml.

The salt is added to the aqueous solution in a quantity and under conditions which are suitable to crystallize the cellulase enzyme. Such conditions, including temperature, pH, concentration of cellulase enzyme, concentration of salt and incubation time, are easily ascertained by one of skill in the art through routine experimentation. However, in a preferred embodiment of the present invention, the salt is added to the aqueous solution in a concentration of between about 0.5% and 10.0% w/v, more preferably between about 1% and 7.5% and most preferably between about 1.5% and 4.0%. The temperature of the aqueous solution after addition of the salt is above 4° C., preferably between about 10° C. and 60° C., more preferably between about 20° C. and 40° C. and most preferably between about 20° C. and 33° C. The pH of the aqueous solution after the addition of the salt is preferably between about 4 and 10, more preferably between about 4 and 9 and most preferably between about 5.5 and 7.8.

Surprisingly, it has been found that crystallization of the cellulase enzyme is facilitated when the temperature of the aqueous solution is above 4° C. and is preferably above 10° C. As described in the Examples below, crystallization of cellulase is much slower and can have much lower yields when the temperature of the aqueous solution is at 4° C. When the temperature of the aqueous solution is above 4° C., preferably between 10° C. and 60° C., more preferably between 20° C. and 40° C. and most preferably between 20° C. and 33° C., crystallization can take place in a matter of hours rather than several days. This is contrary to disclosures made regarding enzymes such as glucose isomerase which require low temperatures (i.e., less than 10° C.) for crystallization (U.S. Pat. Nos. 4,699,882 and 5,120,650).

Separation and collection of the crystalline cellulase enzyme from the aqueous solution after incubation can be achieved through any art recognized means for performing such separation. Suitable means include centrifugation, filtration, vacuum filtration and microfiltration.

Although not required, seed crystals can be added to the solution to facilitate improved crystallization kinetics and control reaction rate and crystal size distribution. As is well known in the art, the use of seed crystals results in favorable kinetics of the crystallization and can increase overall yield, depending on the reaction conditions selected. Crystallization can also be improved by providing crystallization vessels having surface properties conducive to crystallization, e.g., having scratches or notches on the inside wall of the vessel, or other properties, as is well known to one of skill in the art. The use of the minimum but effective amount of seed crystals for a given cellulase enzyme solution, considering the size of the operation and process conditions, will be apparent to one of skill in the art and should follow as in conventional crystallization processes. Crystal growth can be further promoted by providing gentle agitation of the crystallization vessel.

Crystalline cellulase produced by the method of the present invention can be used in a detergent composition or a stonewashing composition according to methods well known in the art. Further, crystalline cellulase produced by the method of the present invention can be used for the stonewashing of denim fabrics, in the preparation of a feed additive or in food preparation according methods well known in the art.

Another surprising discovery is that the crystalline cellulase enzymes produced according to the present invention results in reduced backstaining in textile applications, such as stonewashing, over other cellulases produced by other methods. Examples of processes utilizing cellulase which will benefit from the present method of purification includes methods for the treatment of textiles described in PCT Publication No. WO 92/06221.

EXPERIMENTAL

EXAMPLE 1

Selective Crystallization of EGIII From *Trichoderma longibrachiatum* Using Ammonium Sulfate, Magnesium Sulfate and Sodium Sulfate An aqueous solution comprising an ultrafiltrate concentrate of a fermentation broth derived from the fermentation of *Trichoderma longibrachiatum* which was penta-deleted for EGI, EGII, CBHI, CBHII and β-glucanase was prepared. Methods for preparing such penta-deleted strains suitable for the present purpose are described in PCT Publication No. 92/06183. Ultrafiltration was carried out with a polysulfone membrane having a 10 Kd molecular weight cut off in a spiral ultrafiltration unit. The resultant cellulase solution was at a concentration of 35–120 ONPC/ml. The ultrafiltrate concentrate was brought to room temperature and the pH adjusted using either 1 N HCl, acetic acid or 1 N NaOH. Sulfate salt (either ammonium sulfate, sodium sulfate or magnesium sulfate) was added by slowly pouring the salt into the beaker up to the desired concentration while stirring. After the salt had been added, the solution was incubated at room temperature for five hours. After incubation, a 10 ml aliquot of the reaction slurry was centrifuged at 3000 rpm for about 15 minutes using a bench top centrifuge (IEC Corp.) The supernatant was decanted into another centrifuge tube. The pellet was resuspended into sodium acetate buffer at a pH of 5.5. The pellets were analyzed for remaining activity compared to the original aqueous solution.

EGIII activity was measured by the o-nitrophenyl cellobioside (ONPC) method.

Reagents 50 mM sodium acetate buffer at pH 5.5 was used as the assay buffer. The substrate solution was 25 mM o-nitrophenyl cellobioside. pH was adjusted with 50 mM glycine at pH 10 at the end of the assay. β-glucosidase inhibitor was 5 mM gluconolactone.

Standards and Sample Preparation

Standard EGIII enzyme solution was diluted 1:10 into 900 microliters of assay buffer and vortexed to produce the standard stock solution. Dilutions of protein were prepared at the level of 1:70, 1:130 and 1:220. The liquid enzyme samples were prepared by diluting with assay buffer to obtain a change in absorbance of between 0.04–0.18 dA/min. The absorbance was used to calculate the enzyme activity based on the standard calibration curve.

Assay Procedure

A Cobas Fara reagent rack was set up as follows: inhibitor was placed in Space B, substrate in space #1 and adjusting buffer in space #2. A sample cup filled with assay buffer was placed in positions 1 and 10 as buffer blanks. Two sample cups were filled for each standard and control and placed in the sample racks between the buffer blanks. The sample cups for each sample were placed in the sample rack following the space #10 blank. Incubations were for 10 minutes at 40° C. Absorbance level data was obtained for each sample and used in calculations as follows: the typical linear range of the standards and properly diluted samples is 0.04–0.18 dA/min with subtraction of the blank rate. The mean for the final absorbance reading was calculated for each standard. control, and sample replicates. The blank readings for each sample rack were averaged. The average blank reading was subtracted from each mean final absorbance reading to obtain a net absorbance for each standard, control and sample. Samples having a net sample absorbance falling within the standard curve were measured. A standard curve of net absorbances vs. enzyme concentration was prepared for the standards. A correlation coefficient of at least 0.999 was obtained.

| Dilution | Enzyme Concentration (ONPC/ml) |
|----------|-------------------------------|
| 220      | 0.209                         |
| 130      | 0.353                         |
| 70       | 0.656                         |

The ONPC/ml value for each liquid control and sample from the standard curve was calculated according to the relationship ONPC/ml=(value from standard curve)(dilution).

(A) This experiment studied the effect of the addition of ammonium sulfate to an aqueous solution comprising cellulase on the crystallization of the cellulase. The ultrafiltrate concentrate was prepared as above to a final cellulase concentration of about 39 ONPC/ml. Ammonium sulfate was at 5.0% w/v. Crystallized EGIII was produced at both a pH of 7.2 and 7.8 at a yield in five hours of 7.5 and 25.1%, respectively.

(B) This experiment studied the effect of the addition of magnesium sulfate to an aqueous solution comprising cellulase on the crystallization of the cellulase. The ultrafiltrate concentrate was prepared as above to a final concentration of about 40 ONPC/ml. Magnesium sulfate was added to concentration of about 5% and the pH adjusted to either 8 or 5. Crystallized EGIII was produced at both a pH of 8 and 5 at a yield in five hours of 11.4% and 4.5%, respectively.

(C) This experiment studied the effect of the addition of sodium sulfate to an aqueous solution comprising cellulase on the crystallization of the cellulase. The ultrafiltrate concentrate was prepared as above to the appropriate concentration. All incubations were performed at room temperature and for a period of 5 hours. Results are provided in Table 1.

TABLE 1

| Trial | Activity ONPC/ml | Salt Concentration Weight Volume (%) | pH of Incubation Before Salt Addition | Pellet Yield Based On Activity |
| --- | --- | --- | --- | --- |
| 1 | 39.3 | 1.5 | 7.2 | 70.0% |
| 2 | 39.3 | 2.5 | 7.2 | 80.6% |
| 3 | 39.3 | 3.5 | 7.2 | 85.6% |
| 4 | 38.4 | 1.5 | 7.8 | 64.7% |
| 5 | 38.4 | 2.5 | 7.8 | 92.2% |
| 6 | 38.4 | 3.5 | 7.8 | 92.0% |
| 7 | 50.4 | 3.5 | 5.5 | 77.4% |
| 8 | 50.4 | 3.5 | 6.0 | 80.0% |
| 9 | 50.4 | 3.5 | 6.5 | 83.7% |
| 10 | 50.4 | 3.5 | 7.2 | 71.0% |
| 11 | 81.6 | 3.5 | 7.2 | 83.0% |

EXAMPLE 2

Selective Crystallization of EGIII From
*Trichoderma longibrachiatum* Using Ammonium
Chloride An aqueous solution comprising an ultrafiltrate concentrate of a fermentation broth derived from the fermentation of *Trichoderma longibrachiatum* was prepared as in Example 1. The fermentation was prepared as an ultrafiltrate having a cellulase concentration of 43.2 ONPC/ml and a dry substance content of 8.6%. The ultrafiltrate concentrate was brought to room temperature and ammonium chloride was added at a concentration of 2% w/w by slowly pouring into the beaker up to the desired concentration while stirring. After the salt had been added, the solution was seeded with a small amount of previously prepared EGIII crystal that had been washed twice and reslurried in water and brought to a pH of 6.0 with ammonium hydroxide. The samples were placed in shaker flasks and shaken during incubation at 33° C. Crystal growth was detected after 2 hours using a microscope. After incubation, a 10 ml aliquot of the reaction slurry was centrifuged at 5000 rpm for about 20 minutes using centrifuge (Sorvall Instruments, RC-3B Refrigerated Centrifuge). The pellet was analyzed for remaining activity and contained 59% of the EGIII activity of the original aqueous solution.

EXAMPLE 3

Evaporative Crystallization of EGIII

Ultrafiltrate concentrate of a fermentation broth from the fermentation of *Trichoderma longibrachiatum* as in Example 1 having an activity of about 50 ONPC/ml was subjected to forced evaporation with a vacuum to determine whether spontaneous crystallization could be observed. The pH of the ultrafiltrate concentrate was adjusted to 6.0 with 10% NaOH at room temperature. A Rotavapor Unit RE 121 (Büchi, Switzerland) was used for evaporative distillation. A total of 2260 ml of concentrate was subjected to evaporative distillation to result in a final volume of 660 ml. The residual concentrate weighed 460 g, had a solids content of about 40% and had developed a dark color. The residue was centrifuged for 20 minutes at 4000 rpm in a Technospin R (Sorvall Instruments) to produce a 40% volume/volume pellet and the supernatant decanted. The pellet contained no crystalline cellulase.

EXAMPLE 4

Sodium Sulfate Precipitation of Whole Cellulase From
*Trichoderma longibrachiatumm*

Whole cellulase obtained from a fermentation of *Trichoderma longibrachiatum* was tested to determine if cellulases from *Trichoderma longibrachiatum* which possess cellulose binding domains, EGI, EGII, CBHI or CBHII, would crystallize under conditions suitable for the crystallization of EGIII, which lacks a cellulose binding domain. Ultrafiltrate concentrate was used having a concentration of about 1700 RBB/ml and a pH of 5.0. One aliquot was adjusted to a pH of 7.2 with sodium hydroxide. Five shake flasks at pH 5.0 and five shake flasks at pH 7.2 were filled with 100 ml quantities and 2.5 g, 5.0 g, 7.5 g, 10.0 g or 20 g of sodium sulfate. The flasks were incubated at a temperature of 30° C. and observed at 3, 5 and 24 hours. At each stage of the incubation, an aliquot was withdrawn if a precipitate was observed and spun for 15 minutes at 3000 rpm with the pellet analyzed for crystal content.

A precipitate was observed at 3 hours in the 20% sodium sulfate shake flasks at both pH 5.0 and 7.2. The precipitate was analyzed and found to contain no crystalline cellulase. The quantity of EGIII in whole cellulase is between 1–3% which is insufficient to result in visible crystalline EGIII.

EXAMPLE 5

Sodium Sulfate Precipitation of EGI From
*Trichoderma longibrachiatum*

To confirm the results of Example 4, fermentation broth from a strain of *T. longibrachiatum* which was deleted in cellulases other than EGI was obtained and filter pressed for cell separation. The filtrate contained about 300 RBB/ml which was concentrated to roughly 5X using ultrafiltration to about 1500 RBB/ml. Two parallel series of tests were run under conditions which analyzed crystallization behavior at pH 5.0 and 7.2. Sodium sulfate concentrations of 2.5%, 5.0%, 7.5%, 10.0% and 20.0% were analyzed at each pH level at a temperature of 32° C. After pH adjustment, the salt was added to the concentrated material in shake flasks. Results were analyzed at 3, 5 and 24 hours. No crystal formation was detected by using a microscope at any time.

EXAMPLE 6

Crystallization of *Tirchoderma longibrachiatum*
EGIII with Ammonium Chloride and Sodium
Sulfate at Varying Temperatures An aqueous solution comprising an ultrafiltrate concentrate of a fermentation broth derived from the fermentation of *Tirchoderma longibrachiatum* was prepared as in Example 1. The fermentation was prepared as an ultrafiltrate having a cellulase concentration of 43.2 ONPC/ml and a dry substance content of 8.6%. Four 10 ml samples were made. The pH of the samples was adjusted to 5 to 6 with 10% NaOH. To two of the samples, ammonium chloride was added at a concentration of 2% w/w by slowly pouring into the beaker up to the desired concentration while stirring. To the other two samples, sodium sulfate was added at a concentration of 2% w/w by slowly pouring into the beaker up to the desired concentration while stirring. After the salt had been added, each sample was seeded with a small amount of previously prepared EGIII crystal that had been washed twice and reslurried in water. The samples were placed in shaker flasks and shaken during incubation at 4° C. (one ammonium chloride sample, one sodium sulfate sample) or at 33° C. (one ammonium chloride sample, one sodium sulfate sample). After 22 hours, no crystals formed in the samples incubated at 4° C. while the samples incubated at 33° C. contained crystalline cellulase. After 22 hours, the samples being incubated at 4° C. were incubated at 33° C. At 46 hours, these samples also contained crystalline cellulase. Based on this experiment, it is clear that higher temperatures than those previously used (i.e., 4° C.) result in crystallization. The yields of the four samples are given in Table 2.

TABLE 2

| Crystallizing Agent | Concentration | Temperature | Pellet Yield |
| --- | --- | --- | --- |
| Ammonium Chloride | 2% (w/w) | 4° C. then 33° C. | 59% |
| Ammonium Chloride | 2% (w/w) | 33° C. | 79% |
| Sodium Sulfate | 2% (w/w) | 4° C. then 33° C. | 71% |
| Sodium Sulfate | 2% (w/w) | 33° C. | 68% |

EXAMPLE 7

Selective Crystallization of EGIII From *Tirchoderma longibrachiatum* Using Sodium Formate, Magnesium Acetate, Sodium Sulfate and Combinations Thereof An aqueous solution comprising an ultrafiltrate concentrate of a fermentation broth derived from the fermentation of *Tirchoderma longibrachiatum* was prepared as in Example 1. The fermentation was prepared as an ultrafiltrate having a cellulase concentration of 43.2 ONPC/ml and a dry substance content of 8.6%. Five samples were made containing 3% salt as indicated in Table 3. The pH of the samples was adjusted to 7.2 and the samples were not seeded. The samples were placed in shakers at 31° C. After 20 hours of crystallization, the samples were observed in the microscope. In all samples, crystalline cellulase was observed.

TABLE 3

| Crystallizing Agent | Total Salt Concentration | Temperature |
| --- | --- | --- |
| 1.5% Mg-acetate + 1.5% Na-formate | 3% | 31° C. |
| 1.5% Na-sulfate + 1.5% Na-formate | 3% | 31° C. |
| 1.5% Mg-acetate + 1.5% Na-sulfate | 3% | 31° C. |
| 3% Mg-acetate | 3% | 31° C. |
| 3% Na-formate | 3% | 31° C. |

While the invention has been described in connection with specific embodiments thereof, it will be understood that it is capable of further modifications and this application is intended to cover any variations or adaptations of the invention following, in general, the principles of the invention and including such departures from the present disclosure as come within known or customary practice within the art to which the invention pertains and as can be applied to the essential features hereinbefore set forth, and as follows in the scope of the appended claims.

What is claimed is:

1. A method for the crystallization of cellulase enzyme which lacks a cellulose binding domain comprising:

(a) preparing an aqueous solution containing said cellulase enzyme; and (b) adding to said aqueous solution a salt comprising an anion selected from the group consisting of sulfate, phosphate, formate, acetate, and sorbate, and a cation selected from the group consisting of sodium, potassium, ammonium, magnesium or calcium or a mixture thereof.

2. The method according to claim 1, wherein said anion is selected from the group consisting of sulfate and acetate and said cation is selected from the group consisting of sodium, ammonium and magnesium.

3. The method according to claim 1, wherein said salt comprises sodium sulfate, magnesium sulfate, sodium acetate, or ammonium acetate, under conditions sufficient to crystallize said cellulase enzyme.

4. The method according to claim 1, wherein the mixture is a combination of magnesium acetate and sodium formate, sodium sulfate and sodium formate, or magnesium acetate and sodium sulfate.

5. The method according to claim 1, wherein said cellulase enzyme is derived from a microorganism comprising a filamentous fungus, yeast or bacteria.

6. The method according to claim 1, wherein said salt is added in a concentration of between about 0.5% and 10% w/v.

7. The method according to claim 1, wherein said salt is added in a concentration of between about 1.0% and 7.5% w/v.

8. The method according to claim 1, wherein said salt is added in a concentration of between about 1.5% and 4.0% w/v.

9. The method according to claim 1, wherein said step (b) is carried out at a temperature of between about 20° C. and 40° C.

10. The method according to claim 1, wherein said step (b) is carried out at a temperature of between about 22° C. and 37° C.

11. The method according to claim 1, wherein said step (b) is carried out at a pH of between about 4 and 10.

12. The method according to claim 1, wherein said step (b) is carried out at a pH of between about 5.0 and 7.8.

13. The method according to claim 1, additionally comprising the steps of:

(c) incubating said solution prepared in step (b); and (d) separating the resultant crystalline cellulase.

14. The method according to claim 13, wherein said step (c) is carried out for a time of between about 1 hour and 1 week.

15. The method according to claim 13, wherein said step (c) is carried out for a time of between about 5 hours and 24 hours.

16. The method according to claim 1, wherein said cellulase is present in said aqueous solution in a concentration of between about 10 ONPC/ml and 300 ONPC/ml.

17. The method according to claim 1, wherein said cellulase is present in said aqueous solution in a concentration of between about 10 ONPC/ml and 150 ONPC/ml.

18. A method for separating a cellulase enzyme which lacks a cellulose binding domain from cellulase enzyme which possesses a cellulose binding domain comprising:

(a) preparing an aqueous solution containing said cellulase enzymes; and (b) adding to said aqueous solution a salt comprising an anion selected from the group consisting of sulfate, phosphate, acetate, sorbate, chloride, bromide, fluoride or iodide, and a cation selected from the group consisting of sodium, potassium, ammonium, magnesium or calcium, or a mixture thereof, under conditions sufficient to permit the crystallization of said cellulase which lacks a cellulose binding domain; and (c) separating said crystalline cellulase enzyme which lacks a cellulose binding domain from said aqueous solution containing said cellulase enzyme which possesses a cellulose binding domain.

19. A composition comprising a crystalline cellulase which lacks a cellulose binding domain.

20. A composition comprising a crystalline cellulase which lacks a cellulose binding domain produced according to the method of claim 1.

21. A stonewashing composition comprising the crystalline cellulase produced according to the method of claim 1.

22. A detergent composition comprising the crystalline cellulase produced according to the method of claim 1.

23. A method for the removal of backstaining components from an aqueous solution comprising cellulase enzyme comprising:

(a) preparing an aqueous solution containing said cellulase enzyme;

(b) adding to said aqueous solution a salt comprising an anion selected from the group consisting of sulfate, phosphate, formate, acetate, sorbate, chloride, bromide, fluoride or iodide, and a cation selected from the group consisting of sodium, potassium, ammonium, magnesium or calcium, or a mixture thereof; and (c) separating the resultant crystalline cellulase.

24. A method for the crystallization of cellulase enzyme which lacks a cellulose binding domain comprising:

(a) preparing an aqueous solution containing said cellulase enzyme;

(b) adding to said aqueous solution a salt comprising an anion selected from the group consisting of sulfate, phosphate, formate, acetate, and sorbate, and a cation selected from the group consisting of sodium, potassium, ammonium, magnesium or calcium or a mixture thereof; and wherein said step (b) is carried out at a temperature of between about 10° and 60° C. and a pH of between about 4 and 10; and (c) incubating said solution prepared in step (b) for a time of between about 1 hour and 1 week.

25. A method for the crystallization of a cellulase enzyme lacking a cellulose binding domain comprising:

(a) preparing an aqueous solution containing a cellulase enzyme lacking a cellulose binding domain; and (b) adding to said aqueous solution a salt comprising an anion selected from the group consisting of chloride, bromide, fluoride and iodide, and a cation selected from the group consisting of sodium, potassium, ammonium, magnesium and calcium, wherein step (b) is carried out at a temperature above 4° C. and at a pH of between about 4 and 10.

26. The method according to claim 25, wherein step (b) is carried out at a temperature of between about 10° C. and 60° C.

27. The method according to claim 26, wherein step (b) is carried out at a temperature of between about 20° C. and 40° C.

28. The method according to claim 25, wherein said anion is chloride.

29. The method according to claim 25, wherein the salt is added in a concentration of between about 0.5% and 10% w/v.

30. The method according to claim 25, additionally comprising the steps of:

(c) incubating said solution prepared in step (b); and (d) separating the resultant crystalline cellulase.

31. A composition comprising a crystalline cellulase which lacks a cellulose binding domain produced according to the method of claim 25.

32. A composition comprising a crystalline cellulase which lacks a cellulose binding domain produced according to the method of claim 30.

* * * * *